United States Patent [19]

Weitzner

[11] Patent Number: 5,609,559
[45] Date of Patent: Mar. 11, 1997

[54] DEVICE FOR FEMALE PATIENTS TO PREVENT INVOLUNTARY LOSS OF URINE

[76] Inventor: Howard B. Weitzner, 6729 NW. 29 Way, Fort Lauderdale, Fla. 33309

[21] Appl. No.: 548,642

[22] Filed: Oct. 26, 1995

Related U.S. Application Data

[63] Continuation-in-part of Ser. No. 441,089, May 15, 1995, abandoned.

[51] Int. Cl.$^6$ .................................................. A61F 2/00
[52] U.S. Cl. .................................. 600/29; 600/30; 600/31
[58] Field of Search ........................................ 600/29, 31

[56] References Cited

U.S. PATENT DOCUMENTS 2,638,093  5/1953  Kulick ........................................ 600/31

*Primary Examiner*—Angela D. Sykes
*Assistant Examiner*—Rosiland Kearney
*Attorney, Agent, or Firm*—Robert M. Downey, P.A.

[57] ABSTRACT

An intra-vaginal device includes an anterior inflatable body having a hose extending therefrom and a pressure application zone structured and disposed to direct pressure against the urethra and urethra vesicle junction when inflated, to thereby prevent loss of urine. A posterior portion extends from the inflatable anterior body, terminating at a distal end, and is structured and configured to promote insertion and passage of the device within the vagina. A source of pressurized air is releasably attachable to a distal end of the hose to facilitate inflation of the anterior body.

7 Claims, 2 Drawing Sheets

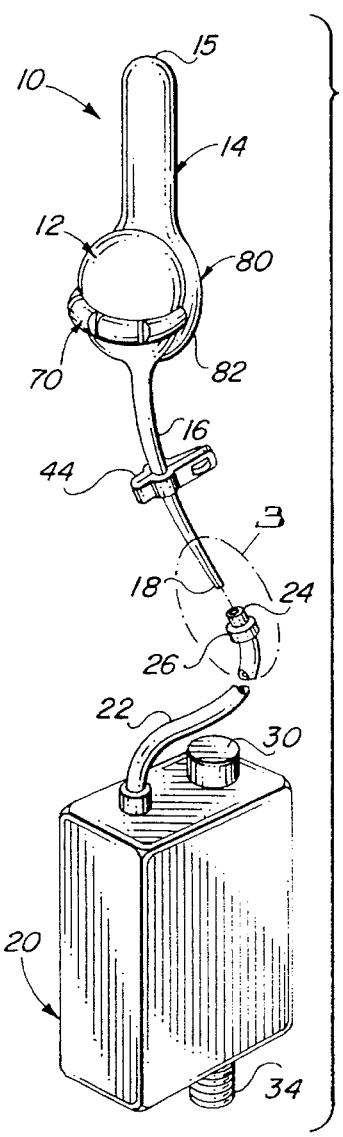
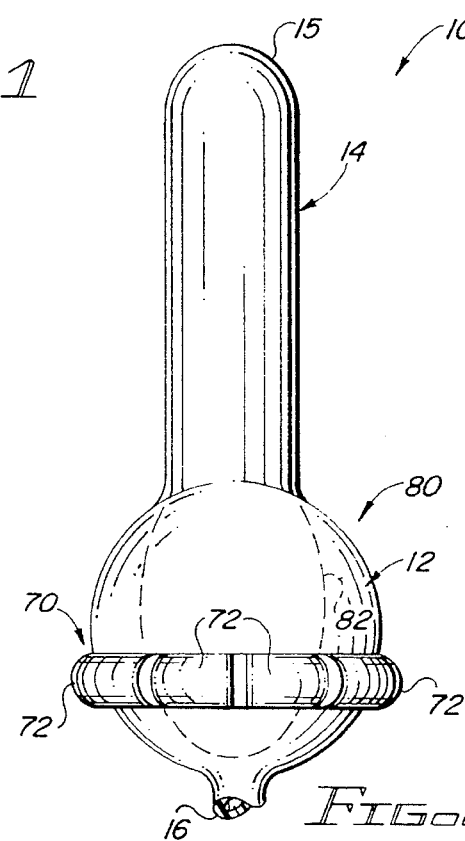
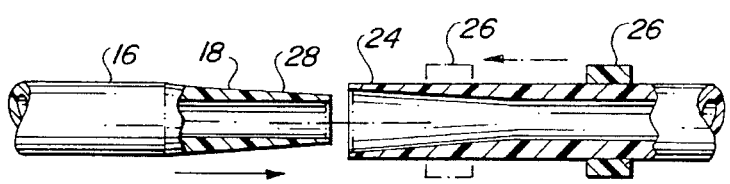
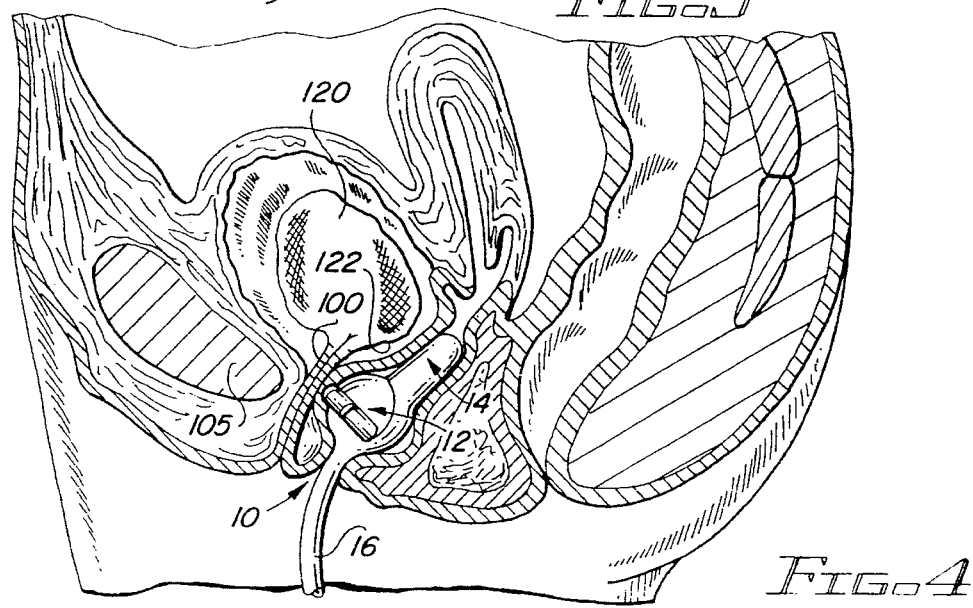

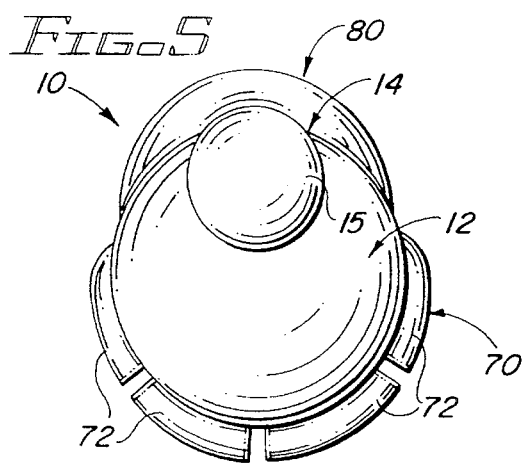
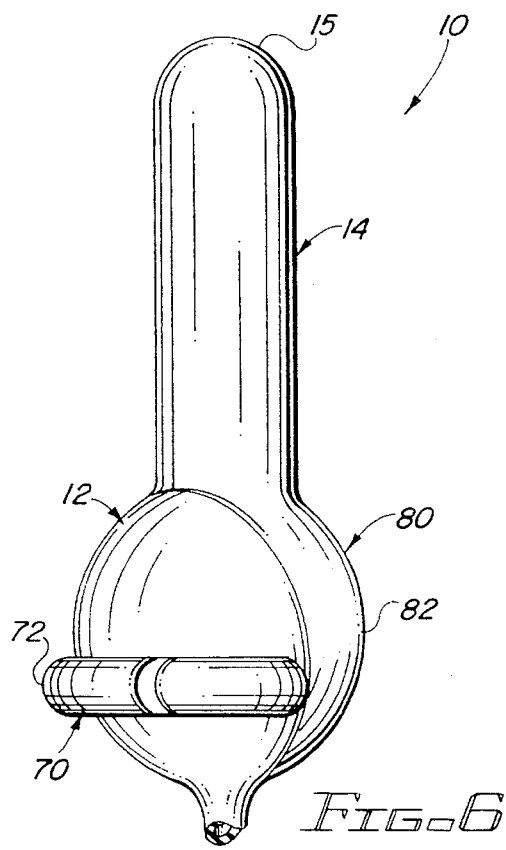
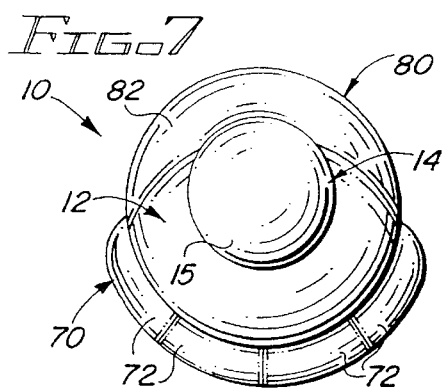
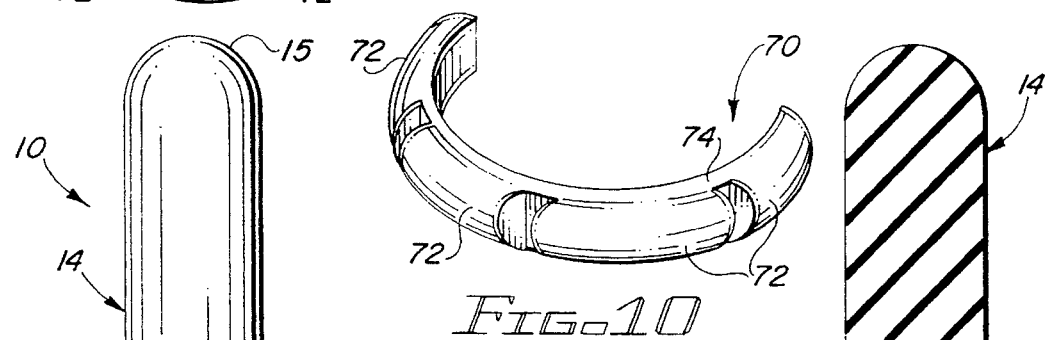
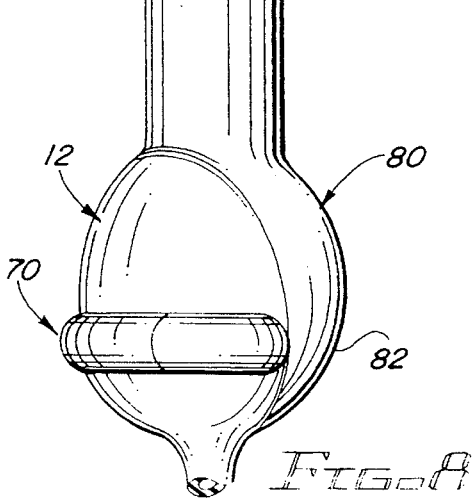
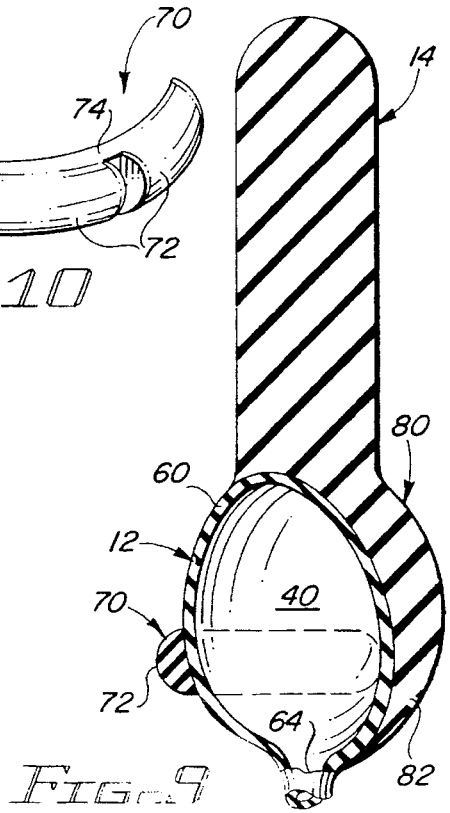

5,609,559

DEVICE FOR FEMALE PATIENTS TO PREVENT INVOLUNTARY LOSS OF URINE

This application is a continuation-in-part application of application Ser. No. 08/441,089 filed on May 15, 1995 now abandoned.

BACKGROUND OF THE INVENTION

1. Field of the Invention

The present invention is directed to a vaginal prosthesis, and more specifically to an inflatable device adapted to be inserted within the vagina to prevent involuntary loss of urine.

2. Description of the Related Art

Urinary stress incontinence is defined as the involuntary, sudden loss of small amounts of urine under sudden increases in intra-abdominal pressure as results from coughing, sneezing, squatting, etc. In genuine or pure stress incontinence, there should be no detrusor muscle activity present, as even slight contractions of the bladder may contribute to loss of urine.

There have been many different operations, drugs, medications, active and passive muscle stimulations, and internal vaginal devices devised and used either singularly or in combination to improve or cure this condition. The problem with each of these modalities is that there is a considerable difference in reported outcomes by different investigators using them. Therefore, there is no agreement amongst authorities as to which one of the many choices is superior. However, most medical experts agree that given a choice between non-surgical and surgical methods, the non-surgical approach should be tried first and, if unsuccessful, then surgery should be considered.

SUMMARY OF THE INVENTION

The present invention is a vaginal prosthesis for the correction of stress incontinence which achieves the same beneficial results as surgery. Specifically, the device of the present invention achieves: 1) elevation of the urethra vesicle junction; 2) increased resting intra-urethral pressure; 3) posterior rotation of the bladder so that the floor of the bladder and not the urethra vesicle junction becomes the most dependent portion of the bladder mechanism in the upright position.

In accordance with the present invention, there is a device containing an anterior inflatable body operable under measured pressure to perform the above functions without causing pressure necrosis of the vaginal mucosa. The anterior body, when inflated to 30 mm of Hg or less, applies pressure to the urethra and the urethra vesicle junction, resulting in elevation and an increase of intra-urethral resting pressure while preventing pressure wounds from forming in the vagina.

A posterior portion extends from the anterior inflatable body and is sized and configured to facilitate insertion and passage of the device within the vagina. With the device properly inserted and inflated, the reduced diameter of the posterior portion relative to the inflated portion allows the floor of the bladder to descend and receive most of the force of intra-abdominal pressure, from coughing, sneezing, or squatting.

Accordingly, with the foregoing summary in mind, it is an object of the present invention to provide a device for controlling involuntary loss of urine and which is specifically structured to achieve: elevation of the urethra vesicle junction; an increase in resting intra-urethral pressure; and posterior rotation of the bladder.

It is a further object of the present invention to provide an intra-vaginal device structured to be inflated once inserted within the vagina and including a pressure application zone specifically structured and disposed to apply pressure against the urethra and the urethra vesicle junction.

It is still a further object of the present invention to provide an intra-vaginal device for controlling involuntary loss of urine which is easily insertable, removable and checkable by the patient for proper positioning in the vagina.

It is still a further object of the present invention to provide an intra-vaginal device which can be used alone for the correction of stress incontinence or as a supplement with other modalities.

It is yet a further object of the present invention to provide a vaginal prosthesis for correction of stress incontinence which is safe and yet which provides the same beneficial results as surgery at a significantly lower cost and health risk to the patient.

These and other objects and advantages of the present invention will be more readily apparent in the description which follows.

BRIEF DESCRIPTION OF THE DRAWINGS

For a fuller understanding of the nature of the present invention, reference should be had to the following detailed description taken in connection with the accompanying drawings in which:

FIG. 1 is a perspective view of the intra-vaginal device of the present invention shown with a handheld pressurized air source adapted to be interconnected to the device for inflation after the device is inserted into the vagina;

FIG. 2 is a front elevation view of the intra-vaginal device;

FIG. 3 is an isolated plan view in partial section illustrating attachment of the hose of the intra-vaginal device to a hose extending from the handheld pressurized air source;

FIG. 4 is a sectional anatomic view showing the device properly positioned within the vagina applying pressure to the urethra vesicle junction;

FIG. 5 is a top plan view of the intra-vaginal device, shown inflated;

FIG. 6 is a side elevation of the intra-vaginal device in the inflated state;

FIG. 7 is a top plan view of the intra-vaginal device, shown in a deflated state;

FIG. 8 is a side elevation of the intra-vaginal device in the deflated state;

FIG. 9 is a side sectional view of the device in the deflated state; and

FIG. 10 is an isolated perspective view of a collar having spaced bulge segments which is fixedly attached to the anterior inflatable body to create a pressure application zone.

Like reference numerals refer to like parts throughout the several views of the drawings.

DETAILED DESCRIPTION OF THE PREFERRED EMBODIMENTS

Referring to the several views of the drawings, there is illustrated the various embodiments of the device, generally indicated as 10, for preventing involuntary loss of urine in women.

Referring initially to FIGS. 1, 2, 6 and 8, a preferred embodiment of the device 10 is shown and includes an anterior inflatable body 12, a posterior aft portion 14 terminating at a blunt distal end 15, and a hose extension 16 extending from the anterior body portion 12. In use, the posterior portion 14 and anterior body 12 are inserted within the vagina with the anterior body in a collapsed, deflated, relaxed state. Once properly inserted and positioned, with the hose 16 extending exteriorly of the vagina, a pressurized air source is connected to the distal end 18 of the hose 16 to inflate the anterior body 12 to a predetermined pressure, preferably not greater than 30 mm of Hg.

In a preferred embodiment, a handheld device 20 is provided, having a pressurized canister or other air pressure cylinder or chamber contained therein. The handheld device 20 includes an air supply hose 22 extending therefrom and terminating at a distal end 24. Referring to FIG. 3, the male distal end 24 of the hose 22 is attachable to a female end 28 on the distal end of the hose extension 16 of the device 10. A sliding collar 26, or like attachment means, facilitates removable attachment of the male 24 and female 28 ends by applying pressure about male end 24 to hold the female end 28 therein. Once attached, a button 30 or other actuation mechanism on the handheld device 20 is operated to release pressurized air flow through the air supply hose 22 and through the attached hose extension 16 into an interior air chamber of the anterior body 12, resulting in inflation thereof to the predetermined pressure, and thus activating the device. A fitting 34 on the handheld device 20 may be provided to facilitate attachment to a compressor or larger air supply for refilling of the pressurized air supply within the chamber of the handheld device 20.

Once the anterior body 12 is inflated to the desired pressure (30 mm of Hg or less), the hose 16 needs to be closed off, prior to disconnection of the air supply hose 22, to prevent deflation of the anterior body 12. This may be accomplished through the use of a clip 44 which releasably clips along the length of the hose extension 16, pinching off the hose and preventing air from escaping from within the interior air chamber. Alternatively, other means may be provided such as a valve fitted in-line along the hose extension 16 and being operable by the patient to close off the air chamber. When it is necessary to remove the device, the clip 44 or other closure means can be removed or opened by the patient, thereby releasing the charge of pressurized air from within the interior air chamber of the anterior body 12, resulting in deflation and at least partial collapse of the anterior body 12. In this manner, the reduced size of the device enables easy removal from within the vagina. A Y-shaped portal with valve means therein is another acceptable closure means.

Referring to FIG. 9, the device 10 is illustrated in cross section (in a deflated state), wherein the anterior body 12 is preferably 3 cm in length and includes an outer wall structure 60, at least partially formed of an impermeable, elastomeric membrane in surrounding relation to the interior air chamber 40 of the anterior body 12. An air passageway 64 is formed at a front end of the anterior body, being integral with the hose extension 16 to define an air passage channel from the distal end of the hose extension 16 to the interior air chamber.

The anterior body 12 is further provided with a pressure application zone 70 specifically structured and disposed to exert a predetermined amount of pressure, preferably 30 mm, against an abutting surface when the anterior body is inflated to the operative state. In FIGS. 2, 5 and 6, the device is shown in the inflated operative state, wherein the interior air chamber is filled with the predetermined charge of pressurized air causing the pressure application zone to bulge outwardly. Accordingly, with the device inserted and properly positioned within the vagina, as seen in FIG. 4, the pressure application zone 70 exerts pressure against the urethra vesicle junction 100 in the direction of the symphysis pubis 105. This serves to elevate the urethra vesicle junction 100, while increasing resting intra-urethral pressure to close off the urethra.

Referring to FIGS. 6, 8 and 9, the posterior portion 14 is integrally attached to the anterior body 12 and extends therefrom. The posterior portion 14 is longer than the anterior body 12, preferably 6 cm in length, and terminates at a distal end 15. The distal end 15 is slightly rounded to eliminate sharp edges. The rounded distal end 15 and elongate configuration of the posterior portion 14 serve to promote travel within the vagina while discouraging damage to the vaginal wall. With the device 10 properly inserted and inflated to the operative state, as seen in FIG. 4, the reduced diameter of the posterior portion 14 relative to the anterior body 12 allows the floor 122 of the bladder 120 to become more dependent and receive most of the increase of intra-abdominal pressure. This also causes posterior rotation of the urethra and bladder.

The anterior body is seated and attached within a partial shell formed of a semi-rigid material and which is integral with the posterior portion 14. The partial shell 80 includes a spoon-shaped portion 82 sized and configured for attached receipt of the anterior body therein so that the spoon-shaped portion is disposed on an exterior of the outer wall structure 60, opposite of the pressure application zone 70. The spoon-shaped portion 82 includes a rounded exterior configuration, integrally formed with said posterior portion 14 to provide a smooth, uninterrupted overall configuration which is compatible with the anatomy of the vagina, thereby promoting insertion and removal of the device 10. The partial shell 80, not being expandable, further serves to direct air pressure upwards within the interior air chamber 40 towards the pressure application zone 70 to promote expansion thereof. Because of the semi-rigid, non-expanding nature of the shell 80, the portion of the outer wall structure 60 of the anterior body 12 which engages the spoon-shaped portion 82 is prevented from expanding outwardly. This serves to promote more definite outward expansion of the pressure application zone 70, as this area of the outer wall structure 60 has less resistance to expansion than the area within the spoon-shaped portion 82.

The spoon-shaped portion 82 is best illustrated in FIGS. 2, 6 and 8 and is specifically shaped and configured to promote insertion and removal of the device for proper positioning within the vagina. It also ensures anterior bulging of the inflatable portion upwards towards the urethra rather than downwards towards the rectum.

Referring to FIGS. 2 and 5–10, and in particular FIG. 10, a preferred embodiment of the pressure application zone 70 is shown to include a collar element 74. The collar element 74 is preferably formed of an elastomeric material and is fixedly attached to the exterior of the outer wall structure 60 of the anterior body 12 using a suitable bonding compound. The collar element is provided with a plurality of spaced bulge segments 72 which are specifically structured and configured to exert concentrated pressure at the urethra vesicle junction. The spacing of the segments 72 allows the collar 74 to expand as the anterior body 12 is inflated to the operative state. The segments 72 are spaced far enough apart so that they will not pinch the vaginal wall when the device is deflated.

The device should be inserted vaginally with the aid of a lubricating jelly such as KY. Another alternative would be an estrogen cream or a mild antiseptic vaginal jelly. A water soluble base is preferred.

While the instant invention has been shown and described in what is considered to be preferred and practical embodiments, it is recognized that departures may be made within the spirit and scope of the invention as set forth in the claims and within the doctrine of equivalents.

Now that the invention has been described,
What is claimed is:

1. An intra-vaginal device for controlling involuntary loss of urine comprising:

an anterior inflatable body including an outer wall structure and a hollow interior air chamber structured to receive a charge of pressurized air to expand said anterior inflatable body from a relaxed, at least partially collapsed state to an operable inflated state to define an enlarged diameter thereof, said anterior inflatable body including an air passage opening disposed in communication with said air chamber, pressure application means on said anterior inflatable body for applying concentrated pressure to an abutting surface when said anterior inflatable body is inflated to said operable state, said pressure application means including at least one bulge segment protruding from said outer wall structure, a posterior portion integral with and extending from said anterior inflatable body and having an elongate configuration with a reduced diameter relative to said enlarged diameter of said anterior inflatable body and terminating at a rounded distal end to promote insertion and passage of said posterior portion and said anterior inflatable body within the vagina, an air passage conduit extending from said air passage opening and terminating at a free distal end, said air passage conduit being structured and disposed to facilitate air flow therethrough into and out from said air chamber, and closure means for selectively and controllingly blocking air flow between said air chamber and said distal end of said air passage conduit to thereby capture said charge of pressurized air within said air chamber, maintaining said anterior inflatable body in said operable inflated state.

2. A device as recited in claim 1 wherein said posterior portion includes an integral partial shell structure formed of a semi-rigid material and including a spoon-shaped portion structured and disposed to receive the anterior inflatable body therein, said spoon-shaped portion having a rounded exterior configuration integrally formed with said elongate configuration of said posterior portion to promote insertion and removal of the device within the vagina and to promote expansion of said anterior inflatable body at said pressure application means.

3. A device as recited in claim 2 wherein said partial shell structure is disposed on an exterior of said outer wall structure of said anterior inflatable body, opposite of said pressure application means.

4. A device as recited in claim 1 wherein said outer wall structure is formed at least partially of a resilient impermeable membrane.

5. A device as recited in claim 4 wherein said closure means includes a clip structured for removable attachment to said air passage conduit, said clip being specifically structured to block air flow through said air passage conduit when attached thereto, thereby preventing air from escaping from within said air chamber.

6. A device as recited in claim 5 wherein said posterior portion includes an integral partial shell structure formed of a rigid material and including a spoon-shaped portion having a rounded exterior configuration integrally formed with said elongate configuration of said posterior portion to facilitate insertion and removal of the device within the vagina.

7. A device as recited in claim 6 wherein said spoon-shaped portion is sized and configured for attached receipt of said anterior inflatable body therein so that said spoon-shaped portion is disposed on an exterior of said outer wall structure of said anterior inflatable body, opposite of said pressure application means, to promote expansion of said anterior inflatable body at said pressure application means.

* * * * *